US010357175B2

(12) United States Patent
De Lucia et al.

(10) Patent No.: US 10,357,175 B2
(45) Date of Patent: Jul. 23, 2019

(54) METHOD FOR PREDICTING AWAKENING IN A COMATOSE PATIENT AND COMPUTER-IMPLEMENTED METHOD THEREOF

(71) Applicant: CENTRE HOSPITALIER UNIVERSITAIRE VAUDOIS (C.H.U.V.), Lausanne (CH)

(72) Inventors: Marzia De Lucia, Lausanne (CH); Athina Tzovara, Lausanne (CH)

(73) Assignee: Centre Hospitalier Universitaire Vaudois(C.H.U.V.), Lausanne (CH)

( * ) Notice: Subject to any disclaimer, the term of this patent is extended or adjusted under 35 U.S.C. 154(b) by 600 days.

(21) Appl. No.: 14/383,165

(22) PCT Filed: Mar. 12, 2013

(86) PCT No.: PCT/EP2013/055036
§ 371 (c)(1),
(2) Date: Sep. 5, 2014

(87) PCT Pub. No.: WO2013/135722
PCT Pub. Date: Sep. 19, 2013

(65) Prior Publication Data
US 2015/0051503 A1  Feb. 19, 2015

Related U.S. Application Data

(60) Provisional application No. 61/609,444, filed on Mar. 12, 2012.

(51) Int. Cl.
*A61B 5/04* (2006.01)
*A61B 5/0484* (2006.01)
(Continued)

(52) U.S. Cl.
CPC ...... *A61B 5/04845* (2013.01); *A61B 5/04012* (2013.01); *A61B 5/4076* (2013.01);
(Continued)

(58) Field of Classification Search
CPC .............. A61B 5/0476; A61B 5/04012; A61B 5/04845
See application file for complete search history.

(56) References Cited

U.S. PATENT DOCUMENTS

2007/0112277 A1* 5/2007 Fischer ................ A61B 5/0006
600/544

FOREIGN PATENT DOCUMENTS

EP  2425769 A1  3/2012

OTHER PUBLICATIONS

Bernard et al., Treatment of Comatose Survivors of Out-of-Hospital Cardiac Arrest With Induced Hypothermia, N Engl J Med, vol. 346, No. 8, pp. 557-563, Feb. 21, 2002.*
(Continued)

*Primary Examiner* — Puya Agahi
(74) *Attorney, Agent, or Firm* — Harness Dickey & Pierce P.L.C.

(57) ABSTRACT

The present invention relates to a method for predicting awakening in a comatose patient based on the progression of auditory discrimination during early stages of coma. EEG measures are acquired from the patient during two distinct periods when said patient is exposed to auditory stimuli comprising repeated standard and deviant sounds. The first period occurs when the comatose patient is in a hypothermia state and the second period occurs when the comatose patient is in a normal temperature state and preferably within 2-3 days from the onset of the coma. The present invention further relates to a computer-implemented method thereof.

19 Claims, 3 Drawing Sheets a. Survivor b. Non-survivor

(51) Int. Cl.
    *A61B 5/00*          (2006.01)
    *G06N 5/04*         (2006.01)
    *A61B 5/0476*     (2006.01)
    *G16H 50/30*      (2018.01)

(52) U.S. Cl.
    CPC .......... *A61B 5/7203* (2013.01); *A61B 5/7275* (2013.01); *G06N 5/04* (2013.01); *A61B 5/0476* (2013.01); *A61B 2505/03* (2013.01); *G16H 50/30* (2018.01)

(56) References Cited

OTHER PUBLICATIONS

Robinson et al., Predictive value of somatosensory evoked potentials for awakening from coma, Crit Care Med 2003, vol. 31, No. 3, pp. 960-967.*

Fugate, J.E., et al. (2010) "Predictors of neurologic outcome in hypothermia after cardiac arrest", *Annals of Neurology*, 68(6):907-914.

Wijnen, V.J.M., et al. (2007) "Mismatch negativity predicts recovery from the vegetative state", *Clinical Neurophysiology*, 118(3):597-605.

International Search Report and Written Opinion dated May 21, 2013 issued in PCT Application No. PCT/EP2013/055036.

* cited by examiner

METHOD FOR PREDICTING AWAKENING IN A COMATOSE PATIENT AND COMPUTER-IMPLEMENTED METHOD THEREOF

PRIORITY STATEMENT

This application is a national stage application under 35 U.S.C. § 371 of PCT International Application No. PCT/EP2013/055036, which has an International filing date of 12 Mar. 2013 and claims priority to U.S. Provisional Patent Application Ser. No. 61/609,444 filed on 12 Mar. 2012. The contents of each application recited above are incorporated herein by reference in their entirety.

FIELD OF THE INVENTION

The present invention relates to a method for predicting awakening in a comatose patient based on his/her improvement in neural auditory discrimination in the early stage of coma. The invention further relates to a computer-implemented method thereof. These methods are for example used in a clinical routine for helping taking therapeutic decisions and optimizing clinical care for each specific patient. In embodiments, the method is implemented in a software embedded in a clinical EEG machine for fast and automatic prediction of patients' chance of surviving.

BACKGROUND ART

Impairment in auditory functions has been repeatedly reported in comatose patients (Fischer et al., 1999) and minimally conscious or vegetative state patients (Boly et al., 2011). Typically, these clinical populations show deficits in neural discrimination between repeated (standard) and rare (deviant) sounds as measured by electroencephalography (EEG) (Näätänen et al., 1978). The degree of discrimination between standard and deviant sounds is quantified by first computing the average of the EEG responses (Auditory Evoked Potentials, AEPs) to standard and deviant sounds. The difference of the average AEPs to the two types of sounds manifests typically at fronto-central electrodes and at ~100-150 ms after the onset of deviation (Fischer et al., 1999; Todd et al., 2007; Wijnen et al., 2007; Garrido et al., 2009) and it is usually referred to as mismatch negativity (MMN) EEG component.

In previous studies on MMN in comatose patients, MMN evaluation requires the identification of a robust average Auditory Evoked Potential (AEP) in response to sounds (i.e. a significant modulation with respect to baseline of the average AEP at about 100 ms post-stimulus onset). Therefore, data from a large percentage of patients are systematically disregarded (e.g. ~33% in one study by Fischer et al., 1999). Furthermore, this assessment requires an a priori hypothesis of the latency and the magnitude of AEP responses. In pathological conditions, making such hypotheses can be challenging, as AEPs can exhibit high inter-individual variability and differ from those of healthy subjects.

Interestingly, MMN appears to be absent in those comatose patients who do not awake from the coma. Therefore, the presence of the MMN is considered to be a predictor of awakening, with high predictive value for awakening (Fischer et al., 2004). However, because this experimental evidence is assessed at various delays after coma onset, it is still unclear whether this deficit is independent of the time of the recording. Moreover, post-anoxic comatose patients are nowadays often treated with mild induced Therapeutic Hypothermia (TH) which is known to have neuro-protective effects on the patients and to increase their chance of survival, but its effect on brain functions remains unknown.

At present, all the tests implemented in the clinical practice are informative of the chance of dying. Specifically, lack of return of brainstem reflexes at 72 hours, early myoclonus, and bilateral absence of early cortical somatosensory evoked potentials (SSEPc) have robust predictive value for death (Bouwes et al., 2009; Fugate et al., 2010; Rossetti et al., 2010).

Therefore, an object of the present invention is to propose a method performed during the very early phase of coma for predicting awakening in a comatose patient treated with TH protocol.

Another object of the present invention is to propose a robust method for predicting awakening in a comatose patient.

Another object of the present invention is to propose a computer-implemented method thereof.

SUMMARY OF THE INVENTION

This invention provides a method for predicting awakening in a comatose patient based on auditory discrimination measured by an electroencephalography machine. This invention has been validated in the context of comatose patients treated with Hypothermia during the first 24 hours of coma. This method comprises the following steps:

a) exposing the comatose patient treated with hypothermia to auditory stimuli within the first 24 hours from the onset of coma, said auditory stimuli comprising repeated standard and deviant sounds;

b) recording the patient's electrical activity in the form of electro-encephalographic data to measure the auditory evoked potential for each standard and deviant sounds of the auditory stimuli while said patient is in hypothermia state and allocating a first value which is informative of the degree of said auditory discrimination;

c) exposing said patient to the same auditory stimuli as in step a) for the second time while in a normal temperature state typically within 72 hours and preferably within 48 hours from the onset of coma;

d) recording the patient's electrical activity in the form of electro-encephalographic data to measure the auditory evoked potential for each standard and deviant sounds of the auditory stimuli while said patient is in a normal temperature state and allocating a second value which is informative of the degree of said auditory discrimination; and e) comparing the first and second values to determine whether there is an improvement of auditory discrimination over time which is informative of whether the comatose patient will awake.

The present invention further provides a computer-implemented method for predicting awakening in a comatose patient based on auditory discrimination. The comatose patient was exposed to auditory stimuli comprising repeated standard and deviant sounds during two distinct periods. The first period occurred when the comatose patient was in a hypothermia state and the second period occurred when the comatose patient was brought back in his/her normal temperature and typically within 72 hours and preferably within 48 hours from the onset of the coma. The comatose patient was equipped with electrodes connected to an electroencephalography machine to record auditory evoked potential (brain responses to each auditory stimulus, hereafter "AEP"), for each standard and deviant sound of the auditory stimuli during the first and second periods. According to the invention the method comprises the following steps:

a. dividing all the recorded AEPs into two datasets, namely a training dataset and a testing dataset;
b. dividing the AEPs from the training dataset into a first and a second category, the first category grouping recorded AEPs in response to standard sounds and the second category grouping recorded AEPs in response to deviant sounds for each of the first and second periods;
c. computing two statistical models of AEPs from the training dataset for standard and deviant sounds respectively and for each of the first and second periods (i.e. eight statistical models of AEPs in total);
d. computing which of the two statistical models of step c) resembles best each of AEPs from the testing dataset for each of the first and second periods;
e. assigning each AEP from the testing dataset to a type of sound, standard or deviant, based on the computation of step d) for each of the first and second periods;
f. determining whether the type of sound assigned to each AEP from the testing dataset is the same as the type of sound that evoked this AEP, in order to conclude if, over all, across all recorded AEPs from the testing dataset for each of the first and second periods, there is a discrimination between standard and deviant sounds above chance level;
g. quantifying the degree of discrimination between standard and deviant sounds for each of the first and second periods in the testing dataset, and
h. comparing the degree of discrimination between standard and deviant sounds between the first and the second period to determine whether there is an improvement of auditory discrimination over time which is informative of whether the comatose patient will awake.

In embodiments of the invention, multivariate Gaussian distribution is applied to compute statistical models of the method.

In embodiments, the degree of auditory discrimination between standard and deviant sounds is quantified by measuring the area under a Receiver Operating Characteristic (ROC) curve.

In embodiments, auditory stimuli comprise one standard and three types of deviant sounds that differ from the standard sound respectively in pitch, in duration and in location, wherein for example steps a) to e) of the above computer-implemented method are preferably performed three times successively for auditory stimuli comprising standard sounds and deviant sounds with respect to pitch, standard sounds and deviant sounds with respect to duration, and standard sounds and deviant sounds with respect to location, respectively, in order to determine a value which is informative of the degree of auditory discrimination of the comatose patient for each type of deviant sounds, and wherein the three values corresponding to each type of deviant sounds are used separately or combined, for example averaged, to obtain one value representing the overall sound discrimination of said patient. In embodiments, auditory stimuli are presented in three successive runs, each run having for example a total of 500 sounds including standard and deviant sounds with respect to pitch, duration and location respectively. Standard sounds represent for example about 70% of the total of sounds, while each of the deviant sounds with respect to pitch, duration and location respectively represents around 10% of the total sounds.

According to the method of the invention, prediction of the awakening in a comatose patient is performed by comparing the responses of said patient to the same or similar auditory stimuli at two distinct moments after the beginning of the coma and in different thermal conditions (hypothermia vs. normothermia). Experiments demonstrated that an improvement of the patient's response over time, from hypothermia to normothermia, was a reliable indication that he or she would eventually awake.

Furthermore, predicting awakening of a patient through a relative data comparison as in the present method, i.e. by comparing data to each other that have been collected from the same patient and in response to the same or similar stimuli, allows for a more robust prediction than methods based for example on the comparison of data collected from a patient to absolute threshold values and/or models that require a higher minimum level of signal for the comparison, and thus for the prediction, to be valid.

DESCRIPTION OF THE FIGURES

The invention will be better understood thanks to the following detailed description with reference to the attached drawings, in which.

DETAILED DESCRIPTION OF THE INVENTION

Figure 1:
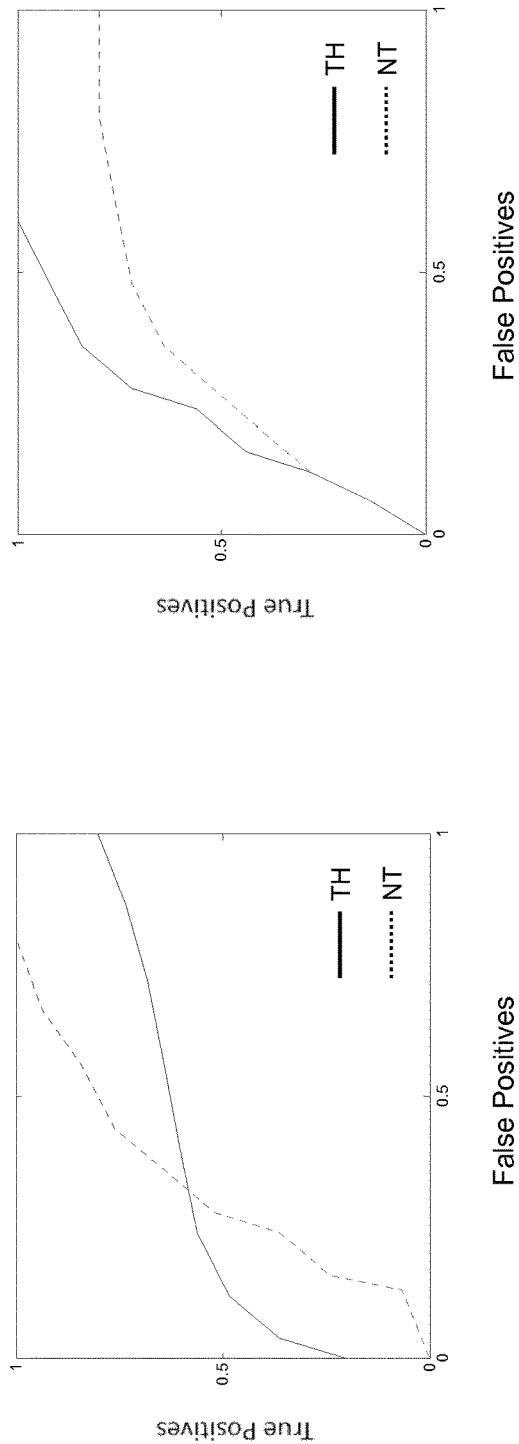
FIG. 1 shows examples of ROC curves plotted according to an embodiment of the invention for an exemplary patient who later awoke (a) and a patient who did not survive the coma (b). ROC curves are the plots of True Positives vs. False Positives when discriminating between two conditions, for example between standard and any type of deviant sounds (here duration deviants). The median ROC curve obtained during the first EEG recording and under TH is displayed in solid lines and the one obtained during the second recording and in NT in dashed lines. For the survivor (panel a), the median Area Under Curve (AUC) in TH was 0.61 and in NT 0.67, leading to an improvement in AUC values of +0.06, which reflects an improvement in auditory discrimination performance. For the non survivor (b), the median AUC in TH was 0.78 and in NT 0.61, leading to a drop of −0.17, reflecting in turn deterioration of auditory discrimination.

The method for predicting awakening in a comatose patient according to embodiments of the invention is based on the evolution of auditory discrimination over time which is informative of the chances that the comatose patient will awake. More specifically, according to this method, the patient, after being resuscitated following current recommendations (2005 American Heart Association Guidelines for Cardiopulmonary Resuscitation and Emergency Cardiovascular Care Circulation 2005:112:IV1-203), is first treated with hypothermia during the first 24 hours of the onset of coma (his/her temperature is lowered for example to about 33 degrees Celsius), a treatment known to produce general neuroprotective effects at early stages of coma (Holzer, 2010).

During a first period, the patient is exposed while in hypothermia state to auditory stimuli comprising a repetitive sequence of sounds. For example, a relatively rare deviant (d) sound can be interspersed among a series of frequent standard (s) sounds (e.g., s s s s s s s s s d s s s s s s d s s s d s s s s ..., where s represents a standard sound and d a deviant sound). The deviant sound can differ from the standard ones in one or more perceptual features such as for example pitch, duration and/or location.

The electrical activity of the patient while exposed to the auditory stimuli is recorded in the form of electro-encephalographic data through an electroencephalography machine to measure the Auditory Evoked Potential (AEP) in response to each standard and deviant sound. A first value quantifying the degree of the auditory discrimination during the first period is then allocated, for example calculated, on the basis of the AEPs recorded during the first period.

The comatose patient is then exposed to the same auditory stimuli during a second period while in a normal temperature state and typically within 72 hours from the onset of coma and preferably within 48 hours. The electrical activity of the patient while exposed to the auditory stimuli is again recorded in the form of electro-encephalographic data through the electroencephalography machine to measure the auditory discrimination. A second value quantifying the degree of the auditory discrimination during the second period is allocated, for example calculated, on the basis of the AEPs recorded during the second period. The first and second values are then compared to each other to determine whether there is an improvement of auditory discrimination over time, which is informative of whether the comatose patient will awake.

The computer-implemented method for predicting awakening in a comatose patient according to embodiments of the invention allows quantifying auditory discrimination on the basis of Auditory Evoked Potentials (AEPs) that are obtained for example as explained above.

The AEPs recorded during each of the first and second periods are randomly divided into two datasets, namely a training dataset including for example 90% of the recorded AEPs and a testing dataset including for example the remaining 10% of the recorded AEPs. Other proportions between the training dataset and the testing dataset are however possible within the frame of the invention.

This data partition allows estimating the statistical models that will be used for evaluating the auditory discrimination on one part of the data (training), and then testing how well this discrimination generalizes to the test dataset (testing).

The AEPs from the training dataset are for example divided into a first and a second category, the first category grouping AEPs recorded in response to the standard sounds of the auditory stimuli and the second category grouping AEPs recorded in response to the deviant sounds of the auditory stimuli, for each of the first and second periods.

If the auditory stimuli comprised more than one type of deviant sounds, the AEPs recorded in response to each type of deviant sound are preferably grouped in a different category. Accordingly, in embodiments, the recorded AEPs are for example separated, for each of the first and second periods, into a first category grouping the AEPs recorded in response to standard sounds of the auditory stimuli, a second category grouping AEPs recorded in response to a first type of deviant sounds of the auditory stimuli, a third category grouping AEPs recorded in response to a second type of deviant sounds of the auditory stimuli, etc.

In embodiments, a statistical model is then computed for the AEPs of each category for each of the first and second periods, respectively. From the training dataset, one statistical model of AEPs is thus for example computed for the response to the standard sounds and one statistical model of AEPs is computed for the response to each type of deviant sounds, and for each of the first and second periods respectively. In embodiments, this for example results in a total of eight different models of AEPs when the auditory stimuli comprised three types of deviant sounds. The statistical models are for example computed using a multivariate Gaussian distribution on the AEPs of each category. This estimation is based on clustering the measured AEPs in response to standard and deviant sounds in few representative configurations of electrical activity. Other methods are however possible within the frame of the invention for computing a model representative of the AEPs of each category.

The AEPs from the testing dataset are then compared to the computed statistical models. For each AEP of the testing dataset for each of the first and second periods, a statistical model which best simulates it is selected. This selection is done for example according to the best fit of the estimated multivariate Gaussian distribution for each of the two conditions. Each AEP from the testing dataset is then assigned to a type of sound for each of the first and second periods and according to the selected model as described above.

The type of sound assigned to each AEP from the testing dataset is then compared with the corresponding type of sound of the auditory stimuli that evoked this AEP, in order to conclude whether there is a discrimination between standard and deviant sounds for each of the first and second periods.

The results of the comparison for each of the first and second periods are then for example represented in the form of a Receiver Operating Characteristic (ROC) curve. The degree of discrimination between standard and deviant sounds for each of the first and second periods is then quantified by measuring the area under the corresponding Receiver Operating Characteristic (ROC) curve. The ROC curve represents a standard measures of performance of discrimination between two conditions and its Area Under Curve (AUC) can range between 0.5 in case of poor discrimination up to 1 for an ideal case. Illustrative but in no ways limiting examples of ROC curves as used within the frame of the invention are shown in FIG. 1.

Finally, according to the method of the invention, the degree of discrimination between standard and deviant sounds between the first and the second period are compared to each other to determine whether there is an improvement of auditory discrimination over time which is informative of whether the comatose patient will awake.

Figures 2A, 2B:
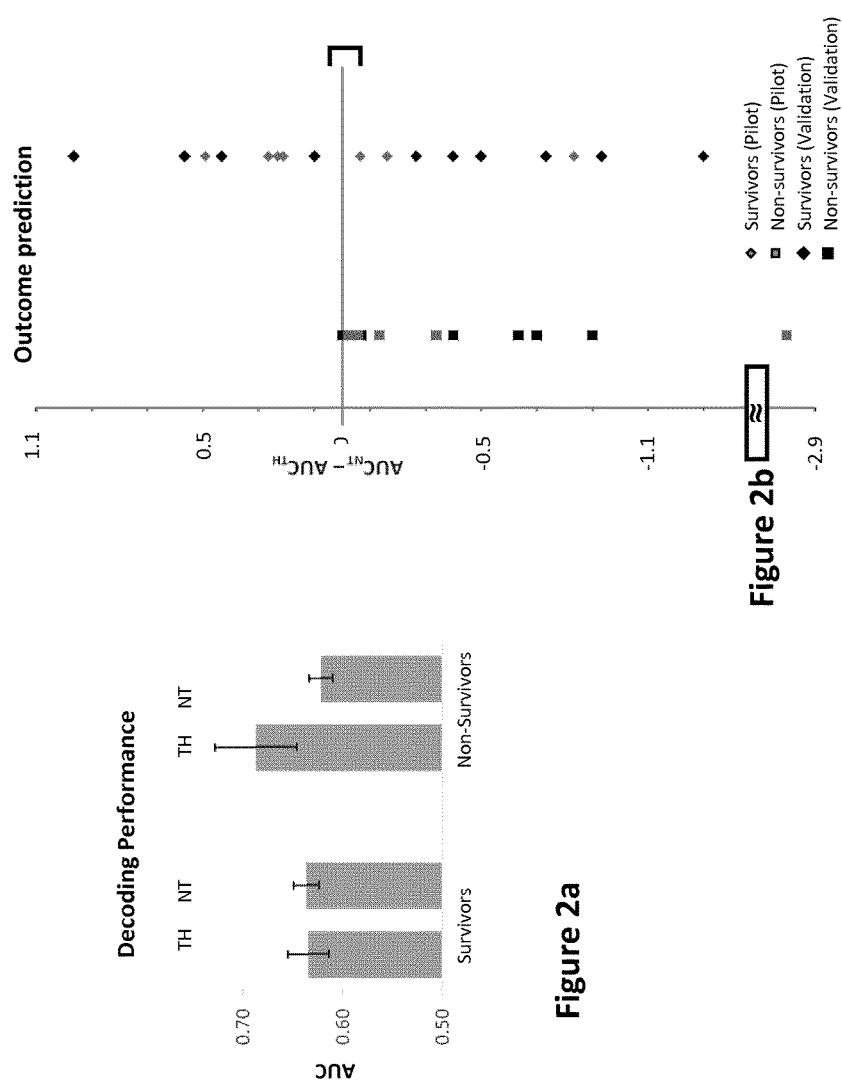
FIG. 2a) represents decoding results obtained by an embodiment of the method of the invention: the graph represents the average decoding performance, with an indication of the standard error mean (s.e.m.), for a pilot group of 12 patients. The decoding performance was measured as the AUC (Area Under Curve) obtained when discriminating responses to standard versus one type of deviant sound (in terms of duration, location or pitch). The decoding performance was averaged across three types of deviant sounds and across patients, under hypothermic (TH) and under normothermic (NT) conditions, respectively. The decoding is especially high for non-survivors and during TH. This decoding performance typically decreases from TH to NT in non-survivors.
FIG. 2b) represents the outcome prediction corresponding to the results of FIG. 1a). The difference in decoding performance from TH to NT—evaluated independently for each patient—is used for predicting the patients' outcome. In the pilot group (grey rhombi and rectangles), an improvement on the average decoding performance from TH to NT conditions is only observed in survivors (rhombi), resulting in a positive predictive value of 100%. All non-awakening patients show a drop in their performance. These results have been replicated on a validation group of 18 patients (panel b, black rhombi and rectangles), whose data analysis was done blindly to their outcome.
Figure 3:
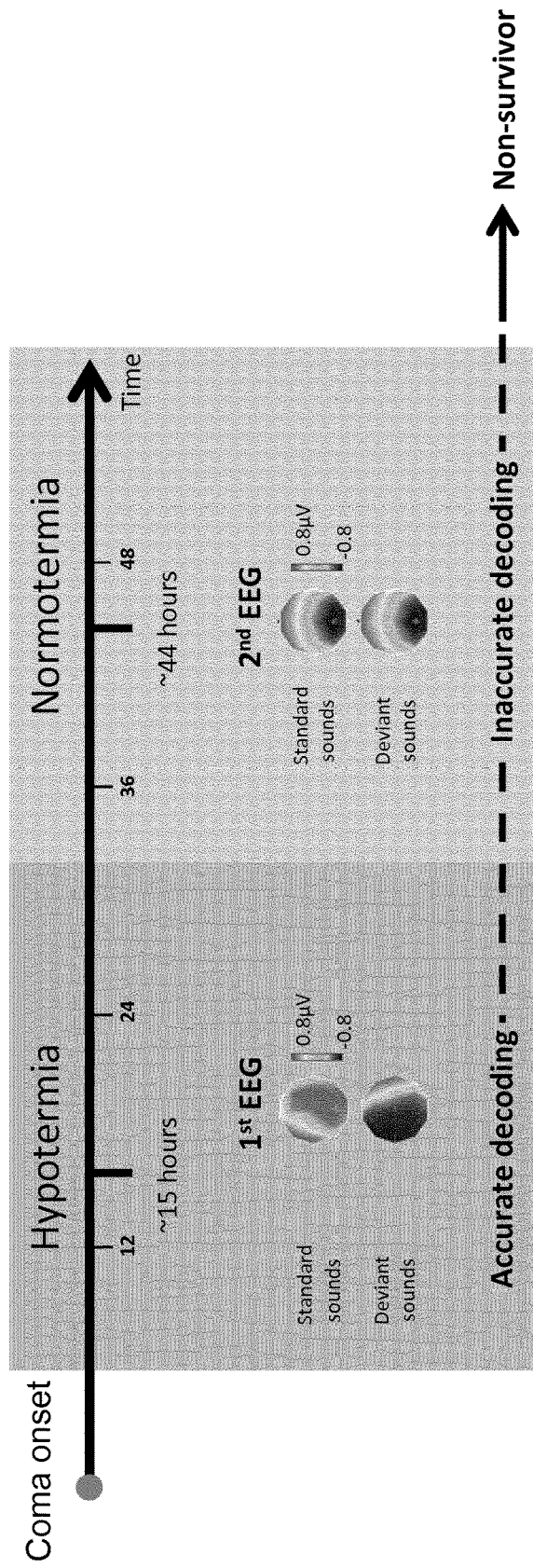
FIG. 3 is a schematic representation of the procedure and exemplary voltage topographies for a patient who did not awake. The first EEG recording was typically performed at about 15 hours after the cardiac arrest, during TH (hypothermia) and the second at approximately 44 hours, after re-warming and under normothermic conditions. A worsening in decoding performance was observed in all the patients who did not awake from coma. Typically, based on the first EEG recording during TH, an accurate decoding performance was obtained which resulted from topographic differences in responses to standard and deviant sounds (voltage topographies estimated by the single-trial model along 100-300 ms post-stimulus onset; left panel). However, during NT, the estimated voltage topographies over the same time window did not differ for the two types of sounds (right panel) and decoding was not above chance. Such a drop in decoding performance was observed in all patients who did not awake from coma.

Applying the method of the invention, successful sound discrimination during early stages of post-anoxic coma and under TH in a large cohort of patients was shown independently of their outcome. Even patients who did not awake from coma exhibited differential patterns of EEG activity in response to standard/deviant sounds (FIG. 2a). Improvement of sound discrimination during the early phase of coma is predictive of awakening and survival at three months, with 100% positive predictive value (FIG. 2b; FIG. 3 for an overview).

The results obtained by the method of the invention show intact auditory discrimination in early phases of coma and even in comatose patients who eventually die and suggest that impairment in neural mechanisms for sound discrimination is a process that occurs over time (FIGS. 1-3). Indeed, the auditory functions can be still intact during the first day after coma onset, largely independent of the patients' final outcome.

The Glasgow coma scale indicated that, during the corresponding analyses, all patients were deeply unconscious during both TH and NT recordings. The high decoding performance during HT and NT provides new evidence about intact auditory functions in a deep unconscious state and during early stages of coma. A possible source of discrepancy with recent literature on intact brain function in comatose patients is the difference in the treatment of these patients (including hypothermia).

At present, in a clinical routine, prognostication of coma after cardiac arrest and TH profits from a multimodal approach. Specifically, lack of return of brainstem reflexes at 72 hours, early myoclonus, and bilateral absence of early cortical somatosensory evoked potentials have robust predictive value for death (Bouwes et al., 2009; Fugate et al., 2010; Rossetti et al., 2010). However, all these tests are not informative of the chance of surviving. The present method thus offers a possibility to bridge the prognostic gap, as it identifies those patients who will awaken in an automatic and quantitative fashion. Moreover, this method provides early and automatic outcome prediction (within ~2-3 days after the coma onset), without disregarding any patient from analysis. Importantly, all analyses were done blindly to patients' outcome and were not used at any point for influencing the clinicians' decision for treatment. Clinicians caring for patients were unaware of the results, so that therapeutic attitudes and decisions were not influenced.

The results obtained by the method of the invention show that early assessment of auditory functions based on EEG multivariate analyses promises to provide a highly informative test of the chance of surviving of comatose patients treated with TH and to largely revise our understanding of intact cerebral functions in deep unconscious state.

EXAMPLE

EEG Data Acquisition 30 post-anoxic comatose patients have been included in the study (10 women; mean age 63±2 years old). They had been admitted from December 2009 to July 2011 to the Department of Critical Care Medicine, Centre Hospitalier Universitaire Vaudois (CHUV-Lausanne University Hospital), Lausanne, Switzerland. All patients were treated with mild TH after resuscitation from cardiac arrest, to 33° C. for 24 hours. The study was approved by the Ethics Committee of the institution.

Level of consciousness was assessed based on the Glasgow Coma Scale (GCS) at regular intervals (every two to three hours) during the first 2-3 days after coma onset. All patients scored 3 or 4 during these first 2-3 days, indicating a deep unconscious state.

All patients were managed according to a standard protocol (Oddo et al., 2006); they were resuscitated following current recommendations (2005 American Heart Association Guidelines for Cardiopulmonary Resuscitation and Emergency Cardiovascular Care. Circulation 2005; 112: IV1-203) and treated with mild TH to 33° C. for 24 hours, using ice-packs, intravenous ice-cold fluids and a surface cooling device (Arctic Sun System, Medivance, Louisville, Colo., USA) for the maintenance of TH, during which midazolam (0.1 mg/kg/h) and fentanyl (1.5 µg/kg/h) were administered for sedation, and vecuronium (0.1 mg/kg boluses) to control shivering.

Patients with myoclonus and/or status epilepticus were treated with intravenous antiepileptic drugs, which were discontinued if no clinical improvement was noted after at least 72 hours. An interdisciplinary decision on withdrawal of intensive care support (Rossetti et al., 2010) was based on a multimodal approach including at least two of the following (assessed in normothermia at least 48-72 hours after cardiac arrest): incomplete recovery of brainstem reflexes, early myoclonus and bilaterally absent cortical somatosensory evoked potentials (SSEP). In particular, results of the present study were not used for this decision. The patients' clinical outcome at three months was categorized as awakening (i.e. beyond a vegetative state) vs. death.

Within the 30 patients, the first 12 (the first 12 admitted to the hospital) formed a pilot group and the rest a validation group. As it will be clear in the following, data from the pilot group were analyzed in a more exploratory manner and results were validated in the validation group (18 patients). All analysis in the validation group was done blindly to the patients' outcome.

Electrodes were set up on the head of each comatose patient and were connected to an EEG machine. Earplugs were inserted in the patient's ears. A script was launched on a computer which was connected to the EEG machine. While the script ran, auditory stimuli comprising standard and deviant sounds were sent to the earplugs and "triggers" were sent to the EEG machine. Triggers are markers that are recorded together with the EEG that can be used to determine when each sound is presented.

The patient was then brought back to his/her normal temperature after about 24 hours from the beginning of the hypothermic treatment. The second EEG recording took place after rewarming and typically within 48 hours from the beginning of the hypothermia. The procedure was identical to the one for the first recording and the same protocol and auditory stimuli were used.

19 electrodes were used for both recordings and were arranged following the international 10-20 system. A sampling rate of 1024 Hz was used with an online reference to the Fpz electrode. All electrodes' impedances were kept bellow 10 kΩ. All EEG recordings were performed in the clinical environment, while patients were lying on their beds, without interrupting the clinical routine. An auditory mismatch negativity paradigm was used for the auditory stimuli. The stimuli comprised one standard and three types of deviant sounds, with a constant inter-stimulus interval of 700 ms. Standard sounds consisted of 1000 Hz sinusoidal tones of 100 ms duration and 0 µs Interaural Time Difference (ITD). The pitch deviant sounds were 1200 Hz sinusoidal tones of 100 ms duration and 0 µs ITD. The duration deviant sounds were 1000 Hz sinusoidal tone of 150 ms duration and 0 µs ITD. Finally, the location deviant sounds were 1000 Hz sinusoidal tones of 100 ms duration and 700 µs ITD (left ear leading). A 10 ms linear amplitude envelope at stimulus onset and offset was applied to all stimuli to avoid clicks. All stimuli were 16 bit stereo sounds sampled at 44.1 kHz. These proprieties were in accordance with other MMN studies (Todd et al., 2008), but other implementations of the auditory stimuli are also possible. A block of trials included 500 stimuli and lasted approximately 7 minutes. Stimuli were presented in a pseudo-randomized order, such that at least one standard stimulus intervened between deviants. 3 blocks were recorded resulting in 1500 trials per participant (1050 for the standard sound and 150 for each type of deviant sound).

EEG Preprocessing

Signal from all electrodes was filtered with a bandwidth filter from 0.1 to 40 Hz in order to reduce artifacts (noise in the signal). Specific parts of the EEG signal, hereafter referred as "single trials", were extracted around each sound starting from −50 ms before the presentation of the sound up to 500 ms after the sound's onset.

Single trials where the EEG signal seemed to be corrupted because of the artifacts were excluded. This was done by excluding single-trials when the voltage measured by any of the electrodes exceeded a threshold of +/−100 µVolts. During the whole recording, signal from each electrode was visually checked on the EEG machine to determine whether any of the electrodes was systematically noisy. In such case, this particular electrode was excluded and its activity was interpolated according to the activity of the neighbour electrodes.

As a result, approximately 100 single trials were obtained in response to each type of sound.

EEG Analysis

The EEG analysis was done on the recording during the hypothermic condition and the normothermic condition separately. Sounds that were presented frequently ('standard sounds', presented about 70% of the single trials), and the other sounds ('rare, or deviant sounds') were compared in order to determine whether there was a statistically significant difference between the EEG responses to one type of sounds and another.

For quantifying the difference in neural responses to standard vs. deviant sounds, a multivariate EEG analysis was used (Tzovara et al., 2013).

The advantage of using this multivariate technique is that it is not biased by a priori hypotheses about electrode location(s) at which stimulus-related activity is expected. Therefore, it is less affected by transient artifact-contaminated activity appearing at some specific electrodes than classical analyses of single-electrode average AEPs. In addition, it provides a way to quantify differences in neural responses at the level of the single patient, without preliminary assessment of minimal inclusion criteria.

This method is based on modelling the voltage topographies of the single-trial AEPs by a Multivariate Gaussian distribution (i.e. mixture of Gaussians, GMM). This analysis was performed separately for each patient and for each of the two recording datasets (i.e. that under TH and that under NT conditions). GMM estimation was based on part of the available trials (Training dataset) and was then used to decode the category of sounds (standard/deviant) on a separate part of the dataset (Test dataset). Decoding performance is indicative of the degree of difference in single-trial brain responses to standard vs. deviant sounds. Importantly, because the analysis is based on voltage topographies, an accurate performance is a direct result of the activation of different neural generators in response to the two sounds categories; a difference in scalp topographies forcibly reflects a difference in the configuration of the underlying generators (Murray et al., 2008). Decoding performance was measured as the area under the Receiving Operating Characteristic curve (AUC—Green and Swets, 1966), with an AUC value of one corresponding to perfect decoding.

Auditory Discrimination in Comatose Patients

In the pilot group of 12 patients, the average decoding performance was high for all patients, irrespective of their outcome and for all three types of deviant sounds (FIG. 2a). The best performance was observed during TH and for non-survivors (FIG. 2a, Non-survivors, TH). Moreover, sound discrimination, based on the decoding performance, was at similar levels between patients who awoke and those who did not, both under TH and NT. Importantly, auditory discrimination as measured by the decoding performance was not predictive of the final patients' outcome neither under TH or under NT (at least at this very early stage of coma).

Prediction of Awakening

By contrast, the change in the AUC from TH to NT was predictive of the patients' outcome in this pilot group (FIG. 2b, y-axis, grey points). An increase in the AUC from first (TH) to second (NT) recording was only observed in survivors (FIG. 2b, grey rhombi), as all patients who did not awake from the coma had unchanged or decreased decoding performance (FIG. 2b, grey rectangles). This result was obtained by averaging the AUC obtained using the three types of deviants as this provided the best prediction of awakening. These first results on the pilot group gave 100% positive predictive value, i.e. all patients with an improvement in the decoding performance from TH to NT awoke from coma and survived at three months.

Validation Group

Data from 18 additional consecutive patients (validation group) were further recorded. All data analysis in this validation group was performed blindly to their outcome, ensuring an objective measure of the predictive value of the method. Results based on this validation group confirmed the observations in the pilot group: an improvement in the decoding performance from TH to NT was only observed in patients awakening from coma and surviving at three months (FIG. 2b, black rhombi and rectangles). Overall, in both groups of patients (pilot and validation) the change of auditory discrimination from TH to NT accurately predicted the clinical outcome for $21/30$ of them (70% accuracy), with 100% specificity (and positive predictive value for awakening and survival at 3 months), and 53% sensitivity. The average decoding performance for survivors, across the three types of deviant sounds, was 0.63±0.01 (mean±s.e.m.) during TH and 0.63±0.01 during NT, while for non-survivors it was 0.67±0.02 during TH and 0.63±0.01 during NT. Moreover, the results provide evidence of intact neural discrimination between standard and deviant sounds during the early phase of coma, largely independent of patients' outcome (FIG. 3 for a summary on the method and our results).

REFERENCES

1. Bekinschtein T A, Dehaene S, Rohaut B, Tadel F, Cohen L, Naccache L. Neural signature of the conscious processing of auditory regularities. *Proc Natl Acad Sci USA* 2009; 106: 1672-7.
2. Boly M, Garrido M I, Gosseries O et al. Preserved feedforward but impaired top-down processes in the vegetative state. *Science* 2011; 332: 858-62.
3. Bouwes A, Binnekade J M, Zandstra D F et al. Somatosensory evoked potentials during mild hypothermia after cardiopulmonary resuscitation. *Neurology* 2009; 73: 1457-61.
4. Fischer C, Morlet D, Bouchet P, Luaute J, Jourdan C, Salord F. Mismatch negativity and late auditory evoked potentials in comatose patients. *Clin Neurophysiol.* 1999; 110: 1601-10.
5. Fischer C, Luauté J, Adeleine P, Morlet D. Predictive value of sensory and cognitive evoked potentials for awakening from coma. *Neurology* 2004; 63: 669-73.
6. Fugate J E, Wijdicks E F, Mandrekar J. Predictors of neurologic outcome in hypothermia after cardiac arrest. *Ann Neurol* 2010; 68: 907-14.
7. Garrido M I, Kilner J M, Stephan K E, Friston K J. The mismatch negativity: a review of underlying mechanisms. *Clin Neurophysiol.* 2009; 120: 453-63.
8. Green D M, Swets J M. Signal detection theory and psychophysics. New York: John Wiley and Sons Inc. 1966.
9. Holzer M. Targeted temperature management for comatose survivors of cardiac arrest. *N Engl J Med.* 2010; 363: 1256-64.
10. Kane N M, Curry S H, Butler S R, Cummins B H. Electrophysiological indicator of awakening from coma. *Lancet* 1993; 341: 688.
11. Murray M M, Brunet D, Michel C M. Topographic ERP analyses: a step-by-step tutorial review. Brain Topography. *Brain Topogr.* 2008; 20: 249-264.
12. Näätänen R, Gaillard A W, Mäntysalo S. Early selective-attention effect on evoked potential reinterpreted. *Acta Psychol (Amst)* 1978; 42:313-29.
13. Oddo M, Schaller M D, Feihl F, Ribordy V, Liaudet L. From evidence to clinical practice: effective implementation of therapeutic hypothermia to improve patient outcome after cardiac arrest. *Crit Care Med.* 2006. 34: 1865-73.
14. Rossetti A O, Oddo M, Logroscino G, Kaplan P W. Prognostication after cardiac arrest and hypothermia: a prospective study. *Ann Neurol.* 2010. 67: 301-7.
15. Todd J, Michie P T, Schall U, Karayanidis F, Yabe H, Näätänen R. Deviant matters: duration, frequency, and intensity deviants reveal different patterns of mismatch negativity reduction in early and late schizophrenia. *Biol Psychiatry* 2008; 63: 58-64.
16. Wijnen V J, van Boxtel G J, Eilander H J, de Gelder B. Mismatch negativity predicts recovery from the vegetative state. *Clin Neurophysiol.* 2007; 118: 597-605.
17. Tzovara A, Rossetti A O, Spierer L, Grivel J, Murray M M, Oddo M, De Lucia M. Progression of auditory discrimination based on neural decoding predicts awakening from coma. 2013; Brain. 136(1):81-9.

The invention claimed is:

1. A method for predicting awakening in a comatose patient based on auditory discrimination measured by an electroencephalography machine, the method comprising the following steps:
    a) providing the comatose patient with intensive care support;
    b) exposing the comatose patient treated with hypothermia to auditory stimuli within the first 24 hours from an onset of coma, said auditory stimuli comprising repeated standard and deviant sounds;
    c) recording by the electroencephalography machine electrical activity of the patient to measure an auditory evoked potential (AEP) for each standard sound and for each deviant sound of the auditory stimuli while said patient is in hypothermia state and allocating a first value which is informative of a degree of said auditory discrimination between the standard sounds and the deviant sounds;
    d) exposing said patient to the same auditory stimuli as in step (b) for a second time while said patient is in a normal temperature state;
    e) recording by the electroencephalography machine the patient's electrical activity to measure the AEP for each standard sound and for each deviant sound of the auditory stimuli while said patient is in the normal temperature state and allocating a second value which is informative of the degree of said auditory discrimination between the standard sounds and the deviant sounds of the auditory stimuli while the patient in in the normal temperature state;
    f) comparing by a computing device the first and second values to determine whether there is an improvement of auditory discrimination over time which is informative of whether the comatose patient will awake;
    g) predicting that, based on the above comparison, the comatose patient will awake when the second value is greater than the first value; and
    h) based on the prediction, continuing the intensive care support.

2. The method according to claim 1, wherein step c) is performed within 72 hours from the onset of coma.

3. A computer-implemented method for predicting awakening in a comatose patient based on auditory discrimination, wherein the comatose patient was exposed to auditory stimuli comprising repeated standard and deviant sounds during two distinct periods including a first period and a second period, the first period occurring when the comatose patient was in a hypothermia state and the second period occurring after the first period when the comatose patient was brought back to his/her normal temperature, the comatose patient having been equipped with electrodes connected to an electroencephalography machine to record auditory evoked potential (AEP) for each standard sound and for each deviant sound of the auditory stimuli during the first and second periods, the method comprising:
    a) dividing, by a computing device, all the recorded AEPs into two datasets, namely a training dataset and a testing dataset;

b) dividing, by the computing device, the AEPs from the training dataset into a first and a second category, the first category grouping AEPs recorded in response to standard sounds of the auditory stimuli and the second category grouping AEPs recorded in response to deviant sounds of the auditory stimuli for each of the first and second periods;

c) computing, by the computing device, two statistical models of AEPs from the training dataset for each standard and deviant sounds respectively and for each of the first and second periods;

d) computing, by the computing device, which of the two statistical models of step c) is a best fit for each of the AEPs from the testing dataset for each of the first and second periods;

e) assigning, by the computing device, each AEP from the testing dataset to a type of sound based on the computation of step d) for each of the first and second periods;

f) determining, by the computing device, whether the type of sound assigned to each AEP from the testing dataset is associated to the corresponding type of sound of the auditory stimuli that evoked each AEP, in order to conclude whether there is a discrimination between standard and deviant sounds for each of the first and second periods;

g) quantifying, by the computing device, the degree of discrimination between standard and deviant sounds for each of the first and second periods;

h) comparing, by the computing device, the degree of discrimination between standard and deviant sounds between the first and the second period to determine whether there is an improvement of auditory discrimination over time which is informative of whether the comatose patient will awake;

i) based on the comparison, determining that there is an improvement of auditory discrimination over time;

j) based on the determination that there is an improvement, determining, by the computing device, within a first 72 hours from an onset of coma that an awakening is expected; and k) based on the determination that an awakening is expected, continuing intensive care support for the comatose patient or treatment of the comatose patient with intravenous antiepileptic drugs.

4. The computer-implemented method according to claim 3, wherein said second period occurs within 72 hours from the onset of coma.

5. The computer-implemented method according to claim 3, wherein a multivariate Gaussian distribution is applied to compute said statistical models.

6. The computer-implemented method according to claim 3, wherein the degree of discrimination between standard and deviant sounds is quantified by measuring an area under a Receiver Operating Characteristic curve.

7. The computer-implemented method according to claim 3, wherein the auditory stimuli comprise one standard and three types of deviant sounds.

8. The computer-implemented method according to claim 7, wherein the three types of deviant sounds differ respectively in pitch, in duration and in location from the standard sound.

9. The computer-implemented method according to claim 8, wherein steps a) to e) are performed three times successively for the auditory stimuli comprising respectively standard sounds and deviant sounds with respect to pitch, standard sounds and deviant sounds with respect to duration and standard sounds and deviant sounds with respect to location in order to allocate a value which is informative of the degree of auditory discrimination of the comatose patient for each type of deviant sounds, and wherein the three values corresponding to each type of deviant sounds are averaged to obtain one value representing the overall sound discrimination of said patient.

10. The computer-implemented method according to claim 9, wherein the auditory stimuli are presented in three successive runs, each run having 500 sounds in total including standard and deviant sounds with respect to pitch, duration and location respectively.

11. The computer-implemented method according to claim 10, wherein standard sounds represents about 70% of the total of sounds of each run, and wherein each of the deviant sounds with respect to pitch, duration and location respectively represents around 10% of the total sounds of each run.

12. The computer-implemented method according to claim 3, wherein two AEP responses of the second category for each type of signal, when present, are averaged in order to reduce signal's noise.

13. The method according to claim 2, wherein step c) is performed within 48 hours from the onset of coma.

14. The computer-implemented method according to claim 4, wherein said second period occurs within 48 hours from the onset of coma.

15. The method according to claim 1, further comprising:
if an awakening expectation is noted, within the first 72 hours from the onset of coma, continuing the intensive care support independent of other test results; and
if an awakening expectation is not noted, determining whether to continue the intensive care support based on the other test results.

16. The computer-implemented method of claim 3, further comprising:
if an awakening expectation is noted, within the first 72 hours from the onset of coma, continuing intensive care support or treatment of intravenous antiepileptic drugs independent of other test results; and
if an awakening expectation is not noted, determining whether to continue intensive care support or treatment of intravenous antiepileptic drugs based on the other test results.

17. A method for predicting awakening in a comatose patient based on auditory discrimination measured by an electroencephalography machine, the method comprising the following steps:
a) treating the comatose patient with intravenous antiepileptic drugs;
b) exposing the comatose patient treated with hypothermia to auditory stimuli within the first 24 hours from an onset of coma, said auditory stimuli comprising repeated standard and deviant sounds;
c) recording by the electroencephalography machine electrical activity of the patient to measure an auditory evoked potential (AEP) for each standard sound and for each deviant sound of the auditory stimuli while said patient is in hypothermia state and allocating a first value which is informative of a degree of said auditory discrimination between the standard sounds and the deviant sounds;
d) exposing said patient to the same auditory stimuli as in step b) for a second time while said patient is in a normal temperature state;
e) recording by the electroencephalography machine the patient's electrical activity to measure the AEP for each standard sound and for each deviant sound of the auditory stimuli while said patient is in the normal temperature state and allocating a second value which is informative of the degree of said auditory discrimination between the standard sounds and the deviant sounds of the auditory stimuli while the patient in in the normal temperature state;

f) comparing by a computing device the first and second values to determine whether there is an improvement of auditory discrimination over time which is informative of whether the comatose patient will awake;

g) predicting that, based on the comparison, the comatose patient will awake when the second value is greater than the first value;

h) determining based on a result of the comparison that an awakening is expected; and i) based on the determination that an awakening is expected, continuing the treatment of the comatose patient with the intravenous antiepileptic drugs.

18. The method of claim 17, further comprising:

within a first 72 hours from the onset of coma, determining, based on the comparison, that an awakening is expected and based on the determination that an awakening is expected within the first 72 hours from the onset of coma, continuing the treatment of the comatose patient with the intravenous antiepileptic drugs.

19. The method of claim 17, further comprising:

if an awakening expectation is noted, within the first 72 hours from the onset of coma, continuing the treatment of intravenous antiepileptic drugs independent of other test results; and if an awakening expectation is not noted, determining whether to continue the treatment based on the other test results.

* * * * *